(12) United States Patent
Zobel et al.

(10) Patent No.: US 9,784,963 B2
(45) Date of Patent: Oct. 10, 2017

(54) STEREO COMPARATOR FOR ASSEMBLY AND INSPECTION OF STEREO ENDOSCOPES

(71) Applicant: Integrated Medical Systems International, Inc., Birmingham, AL (US)

(72) Inventors: Jurgen Zobel, Pembroke Pines, FL (US); Leighton A. Schonlau, Weston, FL (US); Jose A. Ramirez, Hialeah, FL (US)

(73) Assignee: Integrated Medical Systems International, Inc., Birmingham, AL (US)

( * ) Notice: Subject to any disclaimer, the term of this patent is extended or adjusted under 35 U.S.C. 154(b) by 253 days.

(21) Appl. No.: 14/272,049

(22) Filed: May 7, 2014

(65) Prior Publication Data

US 2014/0333721 A1    Nov. 13, 2014

Related U.S. Application Data

(60) Provisional application No. 61/820,232, filed on May 7, 2013.

(51) Int. Cl.
*H04N 13/00* (2006.01)
*H04N 9/47* (2006.01)
(Continued)

(52) U.S. Cl.
CPC ...... *G02B 23/2415* (2013.01); *A61B 1/00057* (2013.01); *A61B 1/00193* (2013.01); *G02B 27/1073* (2013.01); *G02B 27/144* (2013.01)

(58) Field of Classification Search
None
See application file for complete search history.

(56) References Cited

U.S. PATENT DOCUMENTS

2002/0063913 A1* 5/2002 Nakamura ........... G02B 27/017
                                                         359/15
2011/0228049 A1* 9/2011 Kazakevich ......... A61B 1/0005
                                                         348/45
(Continued)

FOREIGN PATENT DOCUMENTS

WO    WO 97/27798    * 8/1997    ............... A61B 1/00

*Primary Examiner* — Hung Dang
(74) *Attorney, Agent, or Firm* — C. Brandon Browning; Maynard, Cooper & Gale, PC

(57) ABSTRACT

A stereo comparator configured for use with a stereo endoscope for adjusting and aligning an optical assembly of the stereo endoscope, for example, in connection with the repair of the endoscope. The comparator includes a housing containing a plurality of optical components, namely, a first deflecting component, a second deflecting component, a third deflecting component and a beam splitter. The optical components are arranged so that the first deflecting component deflects a first beam from a right image channel of a stereo endoscope to the beam splitter, the second deflecting component deflects a second beam from a left image channel of the stereo endoscope to the third deflecting component, the third deflecting component deflects the second beam to the beam splitter and the beam splitter combines the first beam with the second beam to form a first combined beam that extends along an optical axis of the stereo endoscope.

26 Claims, 7 Drawing Sheets

(51) Int. Cl.
*H04N 7/18* (2006.01)
*A62B 1/04* (2006.01)
*H04N 17/00* (2006.01)
*H04N 17/02* (2006.01)
*G02B 23/24* (2006.01)
*A61B 1/00* (2006.01)
*G02B 27/10* (2006.01)
*G02B 27/14* (2006.01)

(56) References Cited

U.S. PATENT DOCUMENTS

2012/0130168 A1* 5/2012 Konomura ......... A61B 1/00009
                                                    600/111
2012/0289843 A1* 11/2012 Chopra ................ A61B 1/0005
                                                    600/508
2014/0364693 A1* 12/2014 Shechterman ..... A61B 1/00193
                                                    600/111

* cited by examiner

STEREO COMPARATOR FOR ASSEMBLY AND INSPECTION OF STEREO ENDOSCOPES

RELATED APPLICATIONS

This application claims priority to U.S. Provisional Application Ser. No. 61/820,232, filed on May 7, 2013, and titled, "Stereo Comparator for Assembly and Inspection of Stereo Endoscopes," the entire contents of which are incorporated herein by reference.

FIELD OF THE INVENTION

The present invention is directed to an apparatus for inspecting the performance of an optical assembly. More particularly, the present invention is directed to stereo comparator configured for use with a stereo endoscope for adjusting and aligning an optical assembly of the stereo endoscope, for example, in connection with the repair of the endoscope.

BACKGROUND OF THE INVENTION

Technical and medical endoscopes are delicate optical instruments that are introduced into technical and human cavities for inspecting the interior of the cavities. Such endoscopes can be rigid endoscopes containing a lens system, flexible endoscopes containing a flexible image guiding bundle or video endoscopes.

Most technical and medical endoscopes are mono endoscopes, though stereo endoscopes have been known in the art since 1904, when Louis & H. Loewenstein received a German patent for a stereo endoscope. Stereo endoscopes are more complex and have a lower brightness than mono endoscope because the cross section available for the optical system of a stereo endoscope is divided between a left image channel and a right image channel. Further, because stereo endoscopes include left optical and right optical channels, those channels must be properly aligned so that the images of the two optical channels overlap within very tight tolerances.

In spite of the complexity and shortcomings of stereo endoscopes, their use has proliferated with the increased demand and execution of minimally invasive surgical procedures, which require handling of surgical instruments under visual control. Mono endoscopes have shown to be poorly configured for such procedures. As a consequence, special endoscopic procedure stereo endoscopes have been developed and in some cases successfully used. The demand for stereo endoscopes has also increased with the advent of robotic surgical procedures and the availability of stereo displays. Because of the rise in use of stereo endoscopes, challenges have arisen in connection with the repair of damaged stereo endoscopes, and particularly, with the inspection, testing and aligning of stereo endoscope optical channels.

More particularly, during assembly of a stereo endoscope optical system, the left optical channel and the right optical channel are evaluated independently to ensure that each optical channel meets certain specified optical parameters and that the quality of the transmitted image for the channel is clear and crisp. Thereafter, the two optical channels are aligned relative to one another. To align the two optical channels, the two optical channels are observed relative to an optimal position. During this alignment, the optical elements that compose the optical trains of the left optical channel and the right optical channel are moved. As a result, the optical parameters and the optical qualities of the two optical channels can change to such a degree that they no longer meet the desired optical parameters. Therefore, it is imperative to control the optical parameters and the optical qualities of the two optical channels, as well as the stereoscopic alignment, of the two channels relative to one another during the alignment process.

Stereo endoscope manufacturers utilize stereo cameras and monitor systems, as part of the stereo endoscopic equipment, to control the optical parameters and the optical qualities of the two optical channels during the alignment and assembly process. Independent service providers who repair stereo endoscopes often do not have access to such stereo cameras and monitor systems. Additionally, hospitals and physicians often do not have access to such equipment when it is desired to inspect and test a stereo endoscope to ensure that the endoscope is proper working condition. This can occur when stereo documentation system of the endoscope manufacturer is not available or the equipment is in use or already sterilized.

Accordingly, there is a need for an optical tool that can be used in conjunction with monoscopic equipment to test and compare the quality of the right and left optical trains that compose a stereo endoscope optical system, as well as the stereoscopic alignment of the two optical systems relative to one another. Such a tool should be simple to use, stably constructed and manufactured at a reasonable cost. Such a tool could be used at several alignment stations in a repair facility, as well as be integrated in a field test kit.

SUMMARY OF THE INVENTION

The present invention is directed to a stereo comparator adapter for stereo endoscopes that can be used as an assembly tool in a repair facility, hospital or surgical clinic. The adapter can be added to existing stationary or portable test equipment for endoscopes. The stereo comparator adapter can be used to control the effects of adjustment and alignment steps of the right and left optical channels of a stereo endoscope. The stereo comparator adapter can also be used during assembly of a repaired stereo endoscope to check if both optical channels are clear and transmit equally crisp images. When the adapter is added to stationary or portable test equipment for endoscopes, the test equipment can be used to test each of the two optical channels independently, as well as to test the stereoscopic alignment of the left and right channels relative to one another. Mono endoscopes can be tested using the adapter using the same equipment and in the same manner described in prior disclosures. Stereo endoscopes are inspected for damage of the shaft and the illumination system in the same manner as mono endoscopes. However, to inspect the optical train of the two optical systems composing the left and right optical channels of a stereo endoscope and the stereoscopic alignment of the two channels relative to one another, the stereo comparator of the present invention can be used.

The stereo comparator adapter is configured to connect to a proximal side of a stereo endoscope. The adapter includes a conventional monoscopic eyepiece through which a stereo endoscopic image transmitted by the stereo endoscope can be observed. The image can be observed in a manner where both optical channels of the stereo endoscope appear overlapped. Additionally, by blocking one of the two optical channels of the stereo endoscope, the image can be observed in a manner where the unblocked channel can be observed and individually inspected.

The adapter utilizes a cubic beam splitter to combine the right and left optical channels. In its most common form, a cube is made from two triangular glass prisms which are glued together at their base using polyester, epoxy, or urethane-based adhesives. A special optical coating on one of the hypotenuse of the glass prism is used, such that half of the light incident through one port, i.e., face of the cube, is reflected and the other half is transmitted. Accordingly, a beam splitter is typically used to separate an optical beam into two optical beams, each of the two optical beams including 50% of the beam intensity and exiting the beam splitter at a right angle relative to one another.

When a beam splitter is used in a reversed mode, two optical beams entering the beam splitter at a right angle relative to one another are combined or overlaid so that two beams exit the beam splitter at a right angle to one another, each of the two beams including 50% of the intensity of the first beam and the second beam. This effect is used in the stereo comparator adapter of the present invention to combine left and right optical channels of a stereo endoscope.

To transmit the two optical beams entering the beam splitter at a right angle relative to one another, the optical axes of the left and right optical channels are deflected towards a common center axis of the stereo endoscope by deflecting the optical axis of one of the optical channels 90° towards the common center axis of the stereo endoscope with a 45° mirror or a 45° prism and deflecting this optical axis with another 45° prism in the direction of the common center axis of the stereo endoscope. The optical axis of the second optical channel is deflected by a 45° prism towards the common center axes of the stereo endoscope. The optical axes of the two optical channels enter the beam splitter at a right angle relative to one another and exit the beam splitter overlaid. The two overlapped beams exit the beam splitter at a right angle, each containing 50% of the intensity of the overlaid beams. The overlaid beam exiting the beam splitter in the direction of the common center axis of the stereo endoscope can be observed through an eyepiece, or if a mechanical adapter is integrated an endoscopic mono camera can be used to observe the overlaid beam.

A mechanical switch can be used to let both optical channels enter the beam splitter. This mechanical switch can be used also in a left or right position to block out one of the channels to enable the inspection of the optical parameters and the clarity and sharpness of the image of the unblocked optical channel.

DETAILED DESCRIPTION OF PRESENTLY PREFERRED EMBODIMENTS

Figure 1:
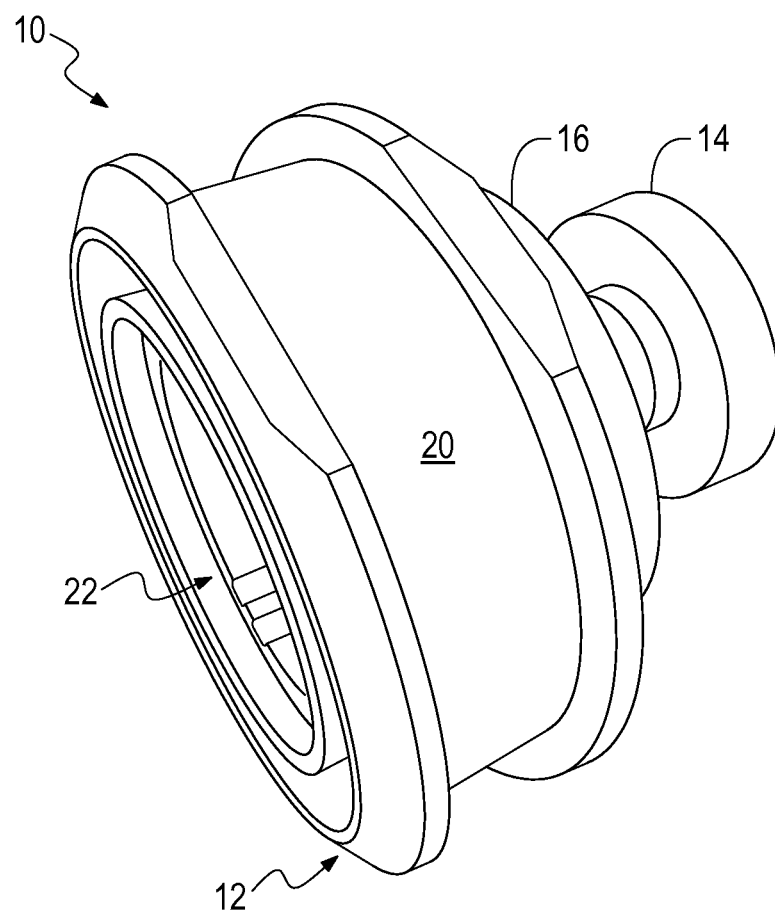
FIG. 1 is a perspective view of stereo comparator adapter in accordance with the present invention showing a distal coupling portion for coupling the adapter to a stereo endoscope and a proximal mechanical eyepiece portion.

The present invention relates to a test and alignment adapter 10 for a stereo endoscope. Generally, adapter 10 includes a distal end including an endoscope coupler portion 12, a proximal end including an eye piece portion 14 and a fixture portion 16 coupled to and between coupler portion 12 and eyepiece portion 14 for supporting an optical assembly 18. When coupler portion 12 is operatively coupled to a stereo endoscope (not shown), optical assembly 18 is arranged to receive right and left channel images from the stereo endoscope, overlay the right and left channel images and transmit the overlaid right and left images through eyepiece portion 14 to a user's eye, a camera or other device capable of displaying the overlaid images for inspection by the user. Further, by selectively blocking transmission of the right channel image and the left channel image, a user can inspect the right and left channel images independently.

Referring to FIG. 1, coupler portion 12 includes a cylindrical body 20 configured for coupling to a proximal end of a stereo endoscope. Cylindrical body 20 includes a central opening 22 into which the proximal end of the stereo endoscope is inserted during use of adapter 10. The design of cylindrical body 20 depends on the design of the proximal end of the stereo endoscope and therefore may vary. In some instances, the proximal end of the stereo endoscope may include an eyepiece so that central opening 22 and cylindrical body 20 are configured for receiving the stereo endoscope eyepiece. To ensure that the right and left channel images transmitted by the stereo endoscope are properly aligned with optical assembly 18, cylindrical body 20 includes means for allowing proper optical alignment there between, the design of such means depending upon the configuration of the proximal end of the stereo endoscope.

Figure 2:
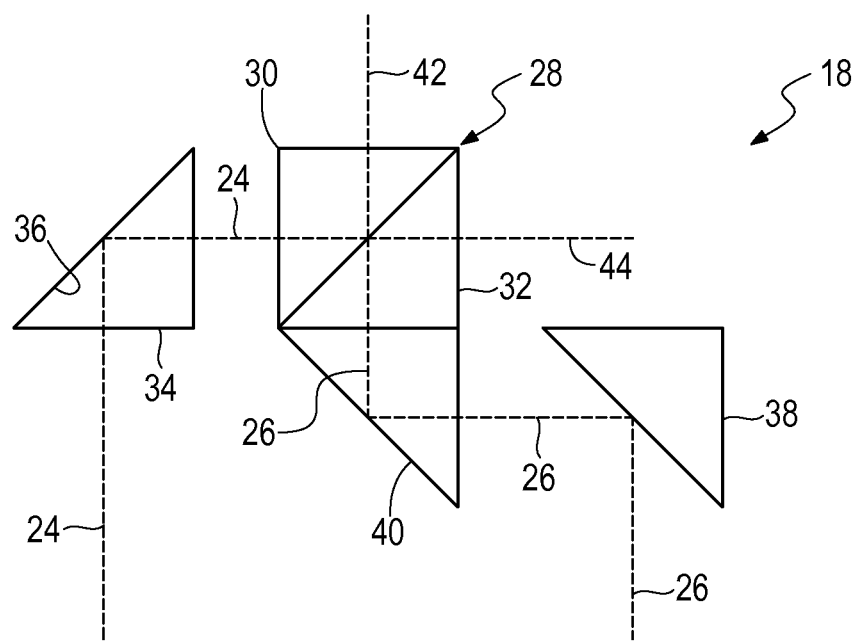
FIG. 2 is schematic drawing of the optical components of the stereo comparator adapter of FIG. 1 depicting the manner in which a left optical axis and a right optical axis of a stereo endoscope are combined into a common optical axis by the optical components.

Referring to FIG. 2, optical assembly 18 is configured for overlaying a right channel image of the stereo endoscope, the right channel image having a right optical axis 24, and a left channel image of the stereo endoscope, the left channel image having a left optical axis 26. Optical assembly utilizes a cubic beam splitter 28 to combine or overlay the right and left channel images. Cubic beam splitter 28 is constructed from two triangular glass prisms 30, 32 which are glued together at their respective bases. A special optical coating on one of the hypotenuse of prisms 30 or 32 is used, such that half of the light incident through one face of beam splitter 28 is reflected and the other half is transmitted. Cubic beam splitter 28 operates by receiving the right and left channel images at a right angle relative to one another and combining the two channel images so that each channel image splits at a right angle, with each split or divided channel image including 50% of the intensity of the right channel image and the left channel image.

To transmit the right and left channel images from the stereo endoscope to cubic beam splitter 28 at a right angle relative to one another, right optical axis 24 and left optical axis 26 of the left and right optical channels, respectively, are deflected towards a common center axis of the stereo endoscope. This is accomplished by deflecting right optical axis 24 at a right angle towards beam splitter 28 and the common center axis of the stereo endoscope with a 45° prism 34 having a mirrored back 36. Similarly, left optical axis 26 is deflected at a right angle towards the common center axis of the stereo endoscope with a 45° prism 38 and then deflected again with another 45° prism 40 in the direction of the common center axis of the stereo endoscope. In this manner, the channel images associated with right optical axis 24 and left optical axis 26 enter cubic beam splitter 28 at a right angle relative to one another and exit cubic beam splitter 28 overlaid as a pair of combined channel images extending along respective optical axes 42, 44. When right and left optical axes 24, 26 of the two channel images are divided and exit cubic beam splitter 28 at a right angle, each resulting overlaid optical axis 42, 44 contains 50% of the intensity of each of the right and the left channel images. Each optical axis 42, 44 can be observed by a user as further described below.

Figure 3:
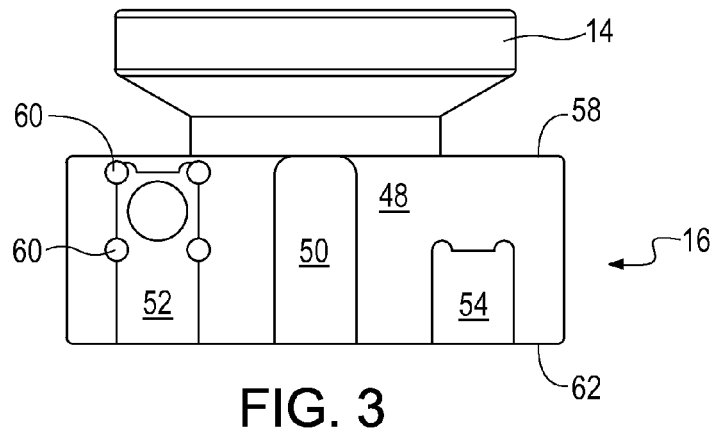
FIG. 3 is an elevational view of the stereo comparator adapter of FIG. 1 (coupling portion not shown) depicting a mechanical fixture portion of the adapter for containing the optical components of FIG. 2.
Figure 4:
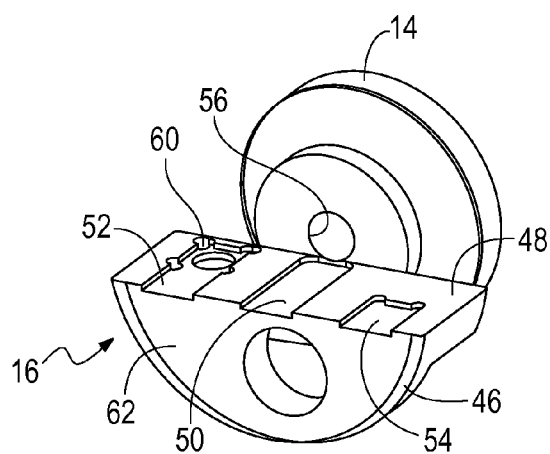
FIG. 4 is a perspective view of a distal side of the mechanical fixture and mechanical eyepiece portions of the stereo comparator adapter of FIG. 3.
Figure 5:
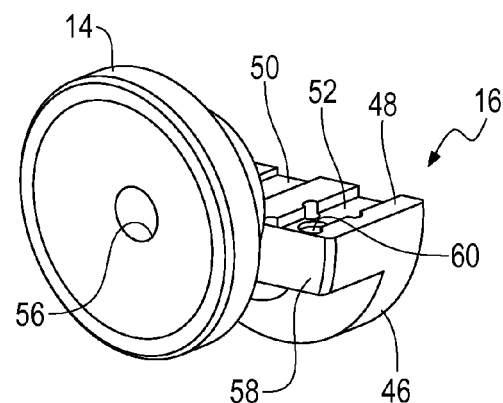
FIG. 5 is a perspective view of a proximal side of the mechanical fixture and mechanical eyepiece portions of the stereo comparator adapter of FIG. 3.
Figure 8:
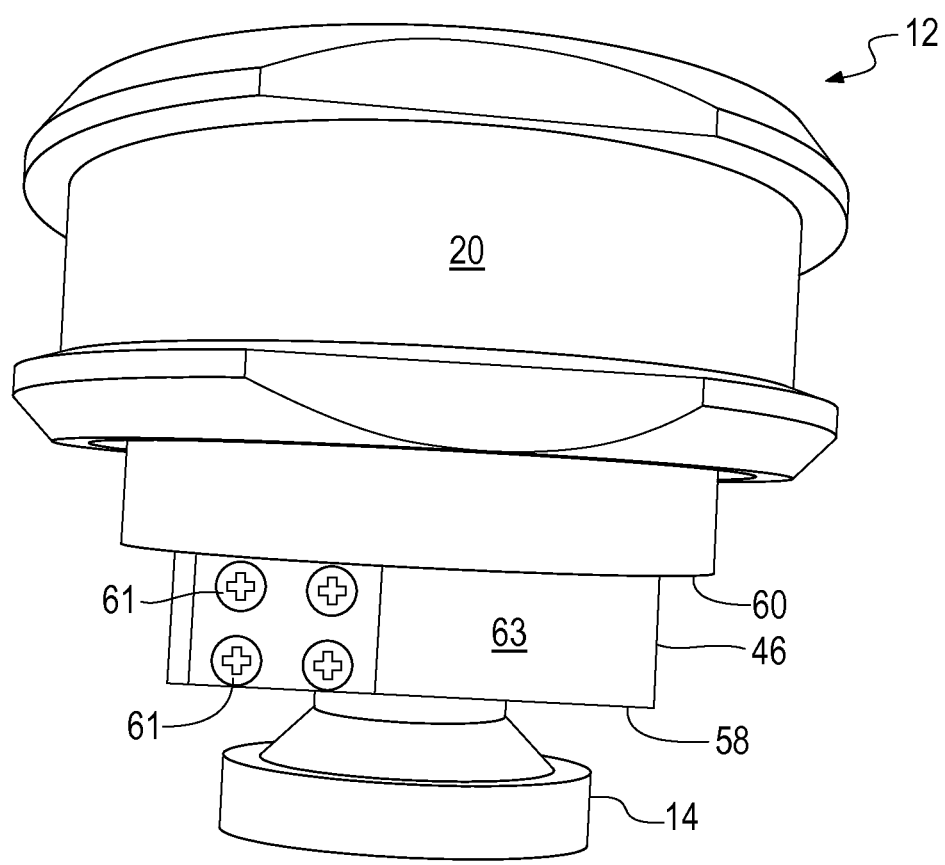
FIG. 8 is a perspective view of the stereo comparator adapter of FIG. 1 showing the configuration of four alignment screws.

Optical components 28, 34, 38 and 40 of optical assembly 18 are maintained in proper optical alignment within adapter 10 by fixture portion 16. Referring to FIGS. 3 through 5, fixture portion 16 is constructed from a semi-cylindrical body 46 having along the diameter thereof a support surface 48 including three groves including a center groove 50, a right groove 52 and a left groove 54, each being configured for receiving respective optical components 28, 34, 38 and 40 of optical assembly 18. In particular, center groove 50 is provided for supporting cubic beam splitter 28 and 45° prism 40 and therefore extends along the central axis of the stereo endoscope and adapter 10. Arranged at the proximal end of central groove 50 and optically aligned therewith is an eyepiece opening 56 through eyepiece portion 14. Eyepiece portion 14 is coupled to a proximal face 58 of semi-cylindrical body 46 with eyepiece opening 56 optically aligned with optical axis 42, cubic beam splitter 28 and the optical axis of the stereo endoscope. Right groove 52 is provided for supporting 45° prism 34 at a location proximal to 45° prism 40. A plurality of screw holes 60 extend through a floor of right groove 52 to enable positioning of 45° prism 34 therein, specifically, for tilting the prism towards the optical axis of the stereo endoscope. As depicted in FIG. 8, screws 61 are inserted through a bottom side 63 of semi-cylindrical body 46 through holes 60 into engagement with 45° prism 34 and can be manipulated to adjust the angle at which 45° prism 34 interacts with cubic beam splitter 28.

Left groove 54 is provided for supporting 45° prism 38 at a location that is distal to 45° prism 34.

Figure 6:
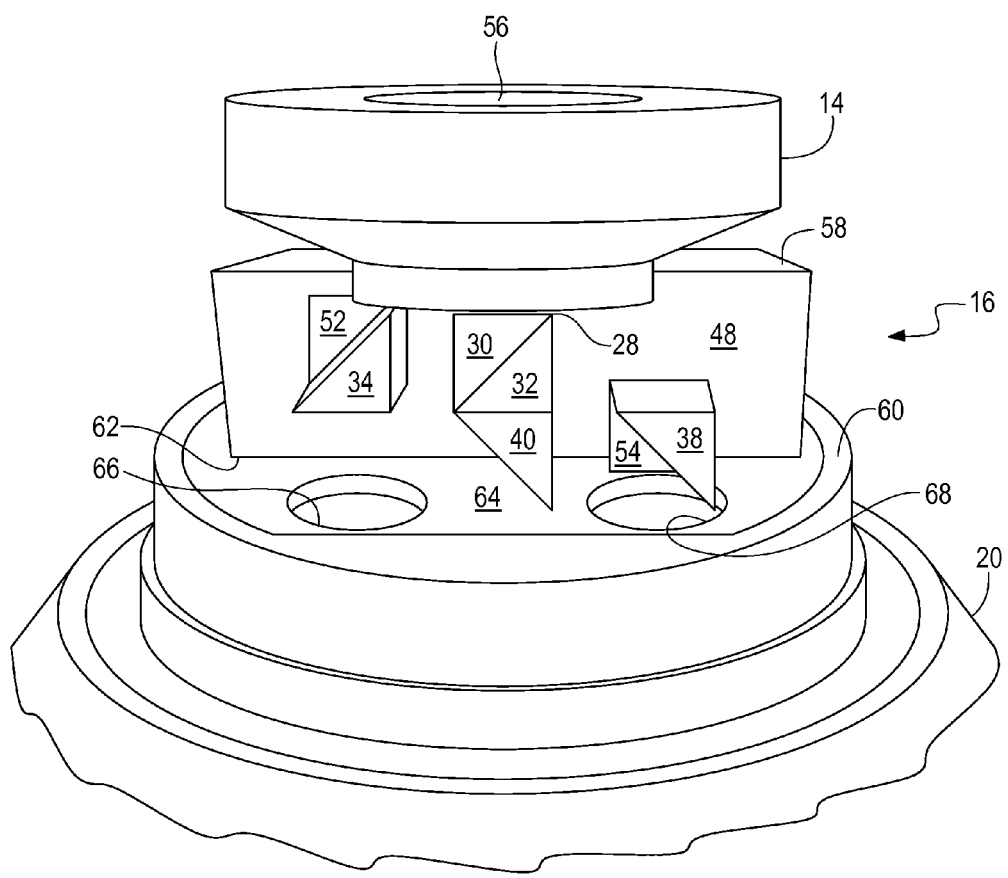
FIG. 6 is a perspective view of the stereo comparator adapter of FIG. 1 showing the arrangement of the coupling, mechanical fixture and mechanical eyepiece portions and the optical components of FIG. 2 contained within the mechanical fixture portion.
Figure 7:
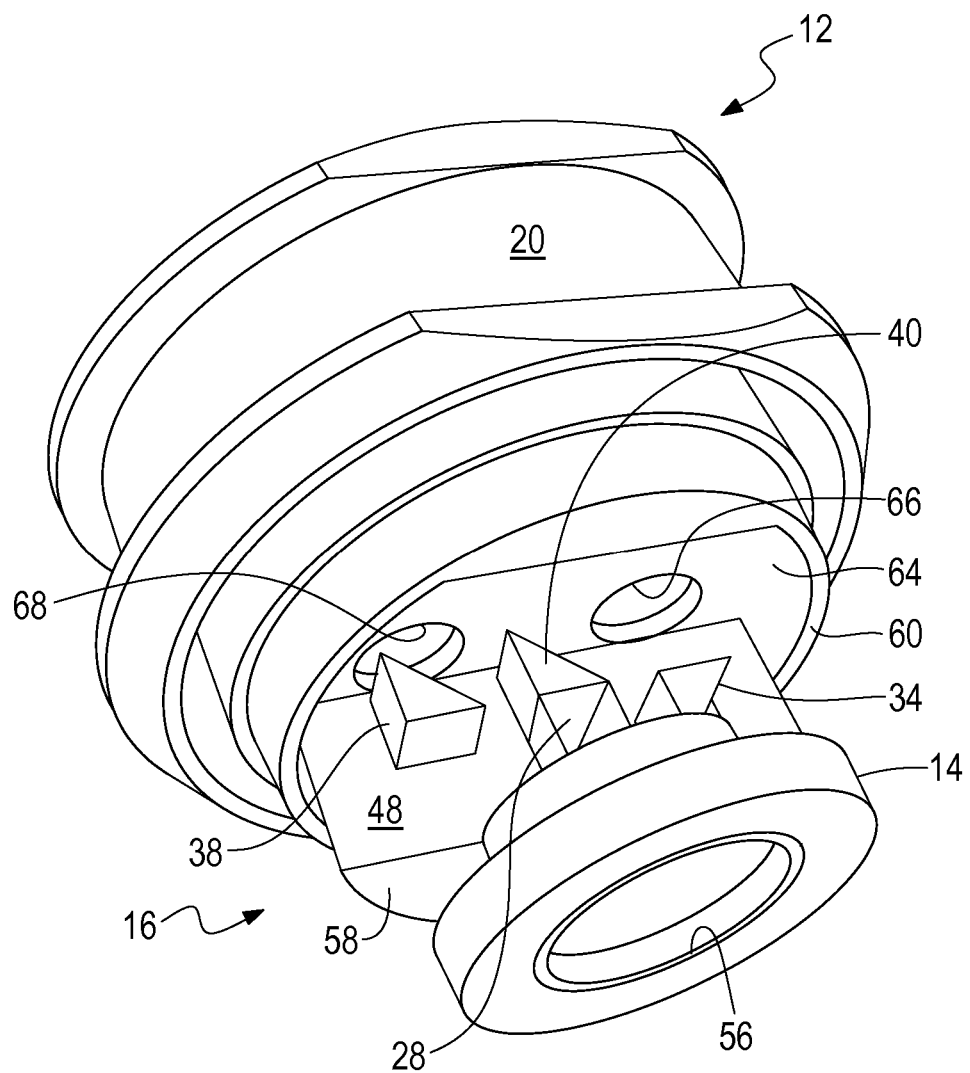
FIG. 7 is another perspective view of the stereo comparator adapter of FIG. 1 showing the arrangement of the coupling, mechanical fixture and mechanical eyepiece portions and the optical components of FIG. 2 contained within the mechanical fixture portion.

Referring to FIGS. 6 through 8, a proximal side 60 of coupler portion 12 is coupled to a distal face 62 of semi-cylindrical body 46 of fixture portion 16. Coupler portion 12 includes a wall 64 located immediately distally to fixture portion 16. Wall 64 includes a right opening 66 and a left opening 68. Coupler portion 12 and wall 64 are arranged relative to fixture portion 16 and optical assembly 18 so that right opening 66 is optically aligned with right optical axis 24 and left opening 68 is optically aligned with left optical axis 26. In this way, the right and left channel images of the stereo endoscope can be transmitted through wall 64 to optical assembly 18 and ultimately through eyepiece opening 56.

Figure 9:
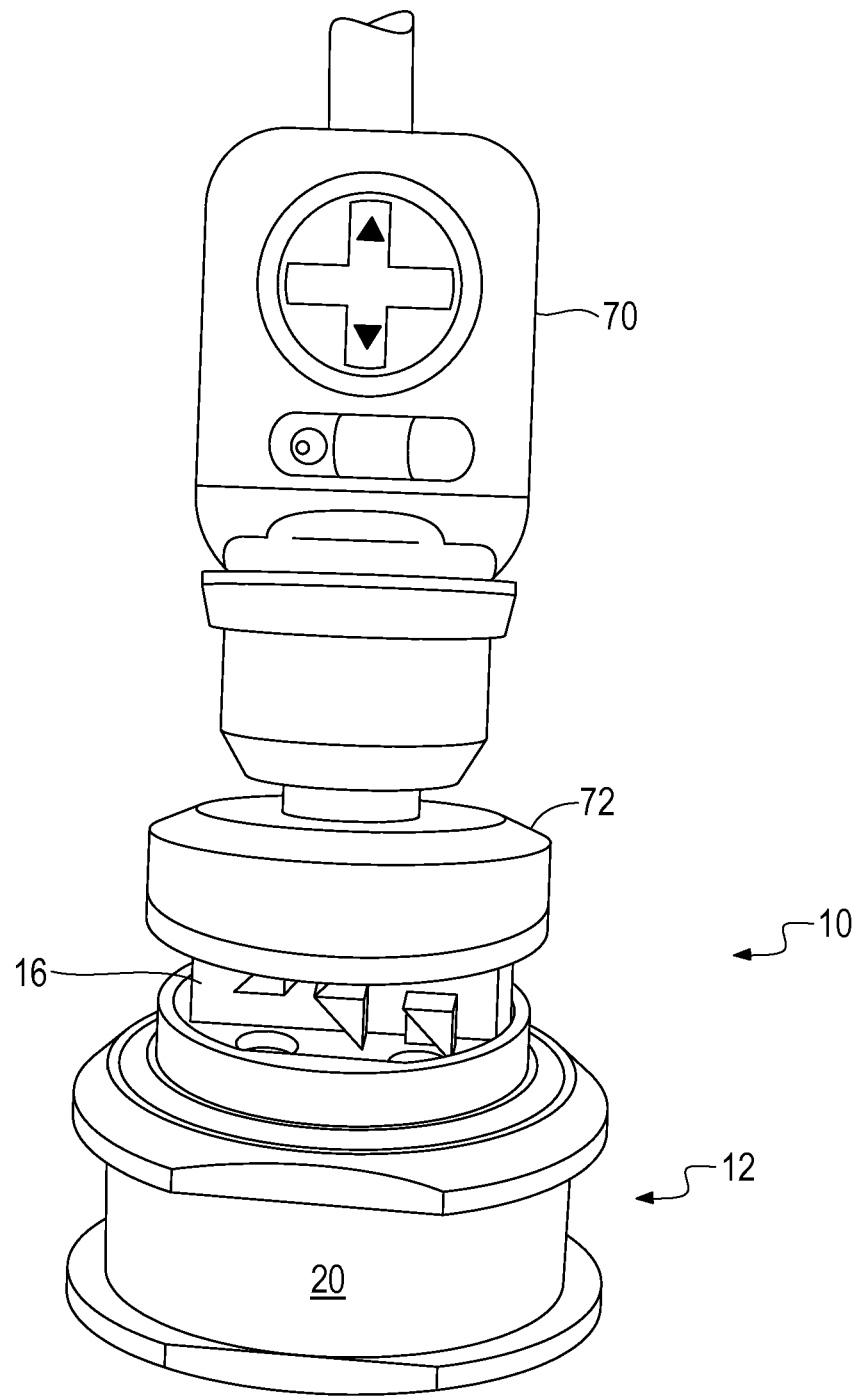
FIG. 9 is a perspective view of the stereo comparator adapter of FIG. 1 coupled to a monoscopic endoscope camera.

Referring to FIG. 9, a monoscopic endoscope camera 70 may be operatively coupled with the proximal side of adapter 10. In this instance, eyepiece portion 14 may be replaced with a camera coupler 72 of conventional design which allows camera 70 to be fixed to and aligned with adapter 10.

Figure 10:
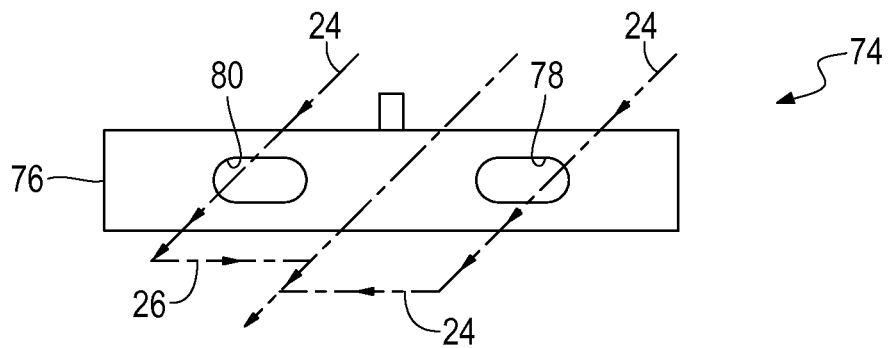
FIG. 10 is a schematic drawing of a mechanical switch for use with the stereo comparator adapter of FIG. 1 in a neutral position for allowing a left optical axis and a right optical axis of a stereo endoscope to be combined into a common optical axis.
Figure 11:
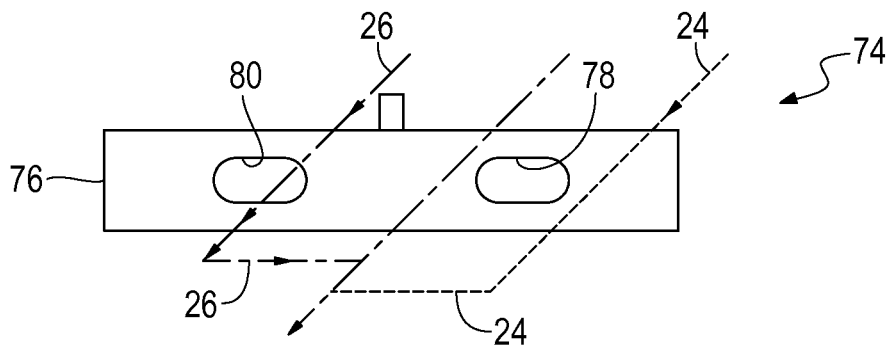
FIG. 11 is a schematic drawing of the mechanical switch of FIG. 10 in a left position.
Figure 12:
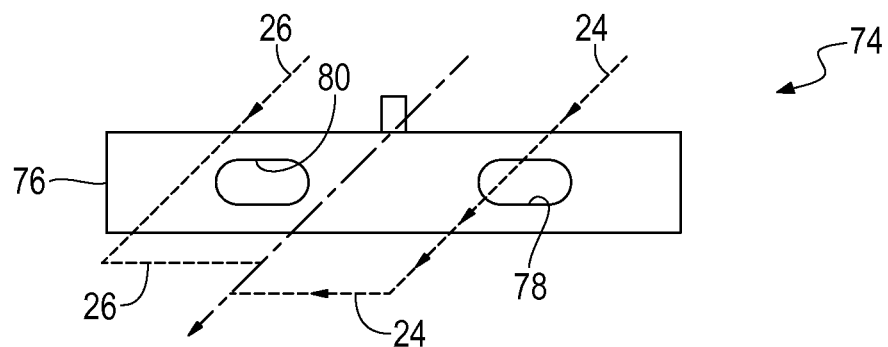
FIG. 12 is a schematic drawing of the mechanical switch of FIG. 10 in a right position.

Referring to FIGS. 10 through 12, there is depicted a switching mechanism 74 for selectively blocking transmission of the right and left channel images of the stereo endoscope to optical assembly 18. Switching mechanism 74 includes an opaque barrier 76 having an elongated right opening 78 and an elongated left opening 80. Preferably, opaque barrier 76 is located immediately proximal to wall 64 of coupler portion 12 and distal to optical assembly 18 and is arranged to slide between a neutral position, as depicted in FIG. 10, a left position, as depicted in FIG. 11 and a right position, as depicted in FIG. 12. It is anticipated that cylindrical body 20 can include a pair of aligned slots for supporting barrier 76 and allowing barrier 76 to selectively move between the neutral, right and left positions. When in the neutral position, the right and left channel images of the stereo endoscope are unblocked and therefore the images of both optical channels can be observed overlaid either visually through eyepiece portion 14 or with the use of monoscopic endoscope camera 70. When in the left position, the right channel image is blocked and therefore only the left channel image can be observed either visually or with the use of the monoscopic endoscope camera. When in the right position, the left channel image is blocked and therefore only the right channel image can be observed either visually or with the use of a monoscopic endoscope camera.

As will be apparent to one skilled in the art, various modifications can be made within the scope of the aforesaid description. Such modifications being within the ability of one skilled in the art form a part of the present invention and are embraced by the claims below.

It is claimed:

1. A comparator comprising:
    a housing having a distal end and a proximal end, the distal end being detachably coupled to a proximal end of a stereo endoscope transmitting out therefrom a first beam and a second beam containing a right image and a left image, respectively,
    a plurality of optical components supported by the housing, the optical components including a first deflecting component, a second deflecting component, a third deflecting component and a beam splitter, wherein the housing and the plurality of optical components do not form part of the stereo endoscope,
    wherein the first deflecting component is arranged to deflect the first beam to the beam splitter, the second deflecting component is arranged to deflect the second beam to the third deflecting component, the third deflecting component is arranged to deflect the second beam to the beam splitter and the beam splitter is arranged to combine the first beam with the second beam to form a first combined beam having a first common optical axis, and an optical opening through the proximal end of the housing through which the combined beam exits the housing and is available for direct observation by a user.

2. The comparator according to claim 1 wherein the first deflecting component is a 45° prism, the second deflecting component is a 45° mirror, the third deflecting component is another 45° prism and the beam splitter is a cubic beam splitter.

3. The comparator according to claim 2 wherein the 45° prisms and the beam splitter have the substantially same base length.

4. The comparator according to claim 2 wherein the 45° mirror is a reflecting back side of a third 45° prism.

5. The comparator according to claim 1 wherein the second deflecting component and the third deflecting component are arranged distally within the housing relative to the first deflecting component and the beam splitter.

6. The comparator according to claim 1 wherein the third deflecting component is arranged to deflect the second beam along the first common optical axis.

7. The comparator according to claim 1 wherein one or both of the first deflecting component and the second deflecting component are adjustably supported by the housing.

8. The comparator according to claim 1 wherein each optical component of the plurality of optical components is manufactured form an optical material with a refractive index that is greater than 1.7.

9. The comparator according to claim 1 wherein the first combined beam includes 50% of the intensity of the first beam and 50% of the intensity of the second beam.

10. The comparator according to claim 1 wherein the beam splitter is arranged to a form a second combined beam having a second common optical axis arranged at a right angle to the first common optical axis.

11. The comparator according to claim 1 wherein the beam splitter is arranged to operate in a reverse mode for combining light beams.

12. The comparator of claim 1 wherein the housing includes an eyepiece through which the combined beam exits through the optical opening.

13. The comparator of claim 1 wherein the housing includes a camera coupler through which the combined beam exits through the optical opening.

14. A field test kit for a stereo endoscope comprising the comparator of claim 1.

15. A method of inspecting an endoscope comprising:
providing an endoscope transmitting out from a proximal end thereof a first optical beam and a second optical beam containing a right image and a left image of an object, respectively,
detachably coupling a stereo endoscope comparator to the proximal end of the endoscope, the stereo endoscope comparator not forming part of the endoscope and including a first optical component, a second optical component, a third optical component and a fourth optical,
aligning the first optical component with a first optical channel of the endoscope, the first optical channel including the first optical beam, wherein the first optical beam is deflected by the first optical component towards the fourth optical component,
aligning the second optical component with a second optical channel of the endoscope, the second optical channel including the second optical beam, wherein the second optical beam is deflected by the second optical component towards the third optical component and by the third optical component towards the fourth optical component, and wherein the fourth optical component combines the first optical beam and the second optical beam into a first combined beam having a first common optical axis, and
observing the first combined beam.

16. The method according to claim 15 further comprising deflecting first optical beam at a right angle towards the fourth optical component.

17. The method according to claim 16 further comprising deflecting the second optical beam at a right angle towards the third optical component.

18. The method according to claim 17 further comprising deflecting the second optical beam at a right angle towards the fourth optical component.

19. The method according to claim 18 further comprising utilizing the fourth optical component to combine the first optical beam and the second optical beam in a manner that forms a second common optical axis that is arranged at a right angle to the first common optical axis.

20. The method according to claim 15 wherein the first optical component is a 45° prism, the second optical component is a 45° mirror, the third optical component is another 45° prism and the fourth optical component is a cubic beam splitter.

21. The method according to claim 15 further comprising arranging the second optical component and the third optical component distally relative to the first optical component.

22. The method of claim 15 comprising using an opaque barrier to selectively block transmission of either the first optical beam or the second optical beam to the fourth optical component.

23. The method according to claim 15 comprising optically aligning a camera with the first common optical axis.

24. The method according to claim 15 comprising repairing and at least partially reassembling the endoscope prior to aligning the first optical component with a first optical channel of the endoscope.

25. The method of claim 15 including observing the first combined beam directly through an eyepiece of the stereo comparator.

26. A method of inspecting an optical assembly of an endoscope comprising:
providing an endoscope transmitting out from a proximal end thereof a first optical beam and a second optical beam containing a right image and a left image of an object, respectively,
detachably coupling a stereo comparator to the proximal end of the endoscope, wherein the stereo comparator does not form part of the endoscope, receives the first optical beam and the second optical beam from the endoscope, combines a portion of the first optical beam with a portion the second optical beam to form a combined optical beam containing an overlaid image composed of the right image and the left image and transmits out from the stereo comparator the overlaid image, and observing the overlaid image.

* * * * *